US00PP22236P2

(12) United States Plant Patent
Tsukahara et al.

(10) Patent No.: US PP22,236 P2
(45) Date of Patent: Nov. 8, 2011

(54) ***PETUNIA* PLANT NAMED 'DAIICHI BLUETTE PURPLE2'**

(50) Latin Name: ***Petunia* hybrid**
Varietal Denomination: Daiichi Bluette Purple2

(75) Inventors: Jun Tsukahara, Yame (JP); Kuniyoshi Konishi, Okayama (JP)

(73) Assignee: Daiichi Engei Co. Ltd

( * ) Notice: Subject to any disclaimer, the term of this patent is extended or adjusted under 35 U.S.C. 154(b) by 66 days.

(21) Appl. No.: 12/660,101

(22) Filed: Feb. 18, 2010

(51) Int. Cl.
*A01H 5/00* (2006.01)

(52) U.S. Cl. ..... Plt./356.18

(58) Field of Classification Search ..... Plt./356.18
See application file for complete search history.

*Primary Examiner* — Kent L Bell

(57) ABSTRACT

A new and distinct *Petunia* cultivar named 'Daiichi Bluette Purple2' is disclosed, characterized by distinctive vibrant purple flowers and a trailing plant habit. The new variety is a *Petunia*, suitable as an outdoor garden or container plant.

1 Drawing Sheet

Figure 1:
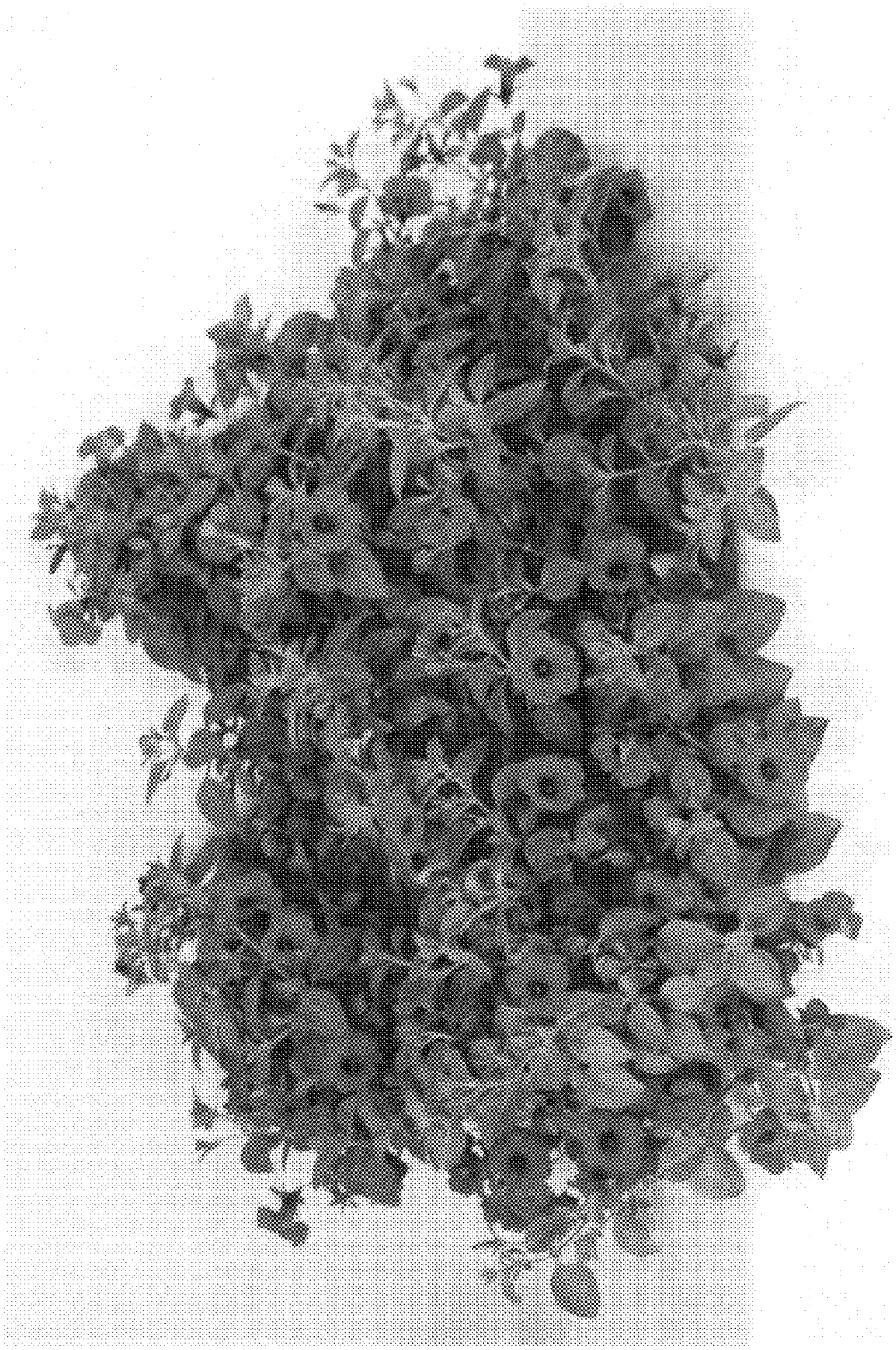

Latin name of the genus and species: *Petunia* hybrid.

Variety denomination: 'Daiichi Bluette Purple2'.

The new *Petunia* cultivar resulted as part of a planned breeding program by the inventors Jun Tsukahara, and Kuniyoshi Konishi, in Yame, Fukuoka, Japan. The objective of the breeding program was to develop new *Petunia* varieties with interesting colors and attractive plant forms.

The new variety resulted from the crossing of the seed parent, an unnamed, unpatented proprietary *Petunia* seedling with the pollen parent, an unnamed, unpatented proprietary *Petunia* seedling in September 2005. The new variety was discovered in November of 2007 by the inventors in a group of seedlings resulting from that crossing, in a commercial greenhouse in Yame, Fukuoka, Japan.

Asexual reproduction of the new cultivar 'Daichi Bluette Purple2' was first performed by vegetative cuttings at a commercial greenhouse in Yame, Fukuoka, Japan in January 2008. Subsequently many generations have been produced and have shown that the unique features of this cultivar are stable and reproduced true to type.

SUMMARY OF THE INVENTION

The cultivar 'Daiichi Bluette Purple2' has not been observed under all possible environmental conditions. The phenotype may vary somewhat with variations in environment such as temperature, day length and light intensity, without however, any variance in genotype.

The following traits have been repeatedly observed and are determined to be the unique characteristics of 'Daiichi Bluette Purple2'. These characteristics in combination distinguish 'Daiichi Bluette Purple2' as a new and distinct *Petunia* cultivar:

1. Distinctive vibrant purple flowers.
2. Trailing Plant Shape.

COMPARISON TO THE PARENT VARIETIES

Plants of the new cultivar 'Daiichi Bluette Purple2' are similar in most horticultural characteristics to plants of the unnamed proprietary seed parent. However, the seed parent has shorter calyx than the new cultivar. Additionally, the seed parent has a less trailing ing and taller plant form than 'Daiichi Bluette Purple2'.

Plants of the new cultivar 'Daiichi Bluette Purple2' are similar in most horticultural characteristics to plants of the unnamed proprietary pollen parent. However, the pollen parent has a different petal form. Additionally, the pollen parent has a less trailing and shorter plant form than 'Daiichi Bluette Purple2'.

COMPARISON TO COMMERCIAL VARIETIES

The new cultivar can be compared to the unpatented commercial variety 'Bluette Purple'. 'Daiichi Bluette Purple2' is similar to this commercial variety in most horticultural characteristics, however, the new variety has an overall taller plant form, with longer stems and more creeping habit.

BRIEF DESCRIPTION OF THE PHOTOGRAPH

The accompanying photograph in FIG. 1 illustrates in full color a typical plant of 'Daiichi Bluette Purple2' grown in a greenhouse, in a 6 inch pot. Age of the plant photographed is approximately 12 weeks from a rooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurement 'Daiichi Bluette Purple2' plants grown in a commercial greenhouse in Oxnard, Calif. The growing temperature ranged from 18° C. to 25° C. The greenhouse is subject to partial shade. General light conditions are bright, normal sunlight with some shade during the brightest part of the day. Measurements and numerical values represent averages of typical plant types.

Botanical classification: *Petunia hybrid* 'Daiichi Bluette Purple2'.

PROPAGATION

Time to initiate roots: About 7 days at approximately 25° C.
Time to develop roots: About 14 to 21 days at approximately 25° C.
Root description: Fine, fibrous.

PLANT

Growth habit: Trailing.
Pot size of plant described: Approximately 6 inch.
Height: Approximately 14 cm from soil line to top of plant.
Plant spread: Approximately 55 cm at widest point.
Growth rate: Rapid.
Branching characteristics: Free branching.
Length of primary lateral branches: Approximately 18 cm.
Quantity of primary lateral branches: Approximately 70.
Characteristics of primary lateral branches:
*Diameter.*—Approximately 0.4 cm.
*Color.*—Near RHS Yellow-Green 144A.
*Texture.*—Pubescent.
*Strength.*—Highly flexible, moderately strong.
Internode length: Approximately 2.8 cm.

FOLIAGE

Leaf:
*Arrangement.*—Opposite.
*Quantity.*—Approximately 18 per main lateral branch.
*Average length.*—Approximately 5.1 cm.
*Average width.*—Approximately 3.2 cm.
*Shape of blade.*—Ovate.
*Apex.*—Acute.
*Base.*—Obtuse.
*Margin.*—Entire.
*Texture of top surface.*—Matte with very slight pubescence.
*Pubescence.*—Very short, less than 1 mm hairs, sparsely covering leaf.
*Aspect.*—Flat to slightly undulate.
*Color.*—Young foliage upper side: Near RHS Green 137B. Young foliage under side: Near RHS Green 137D. Mature foliage upper side: Near RHS Green 137A. Mature foliage under side: Near RHS Green 137C.
*Venation.*—Type: Pinnate. Venation color upper side: Near RHS Yellow-Green 144A. Venation color under side: Near RHS Yellow-Green 144C.
*Petiole.*—Length: Approximately 1 cm. Diameter: Approximately 0.2 cm. Color: Near RHS Yellow-Green 144C. Texture: Slightly pubescent.

FLOWER

Natural flowering season: Spring and Summer.
Days to flowering from rooted cutting: Approximately 50.
Inflorescence and flower type and habit: Single salverform with fused petals.
Rate of flower opening: Approximately 2 to 3 days from bud to fully opened flower.
Flower longevity on plant: Approximately 5 days.
Approximate quantity of flowers per plant: Approximately 200 flowers and buds.
Flowers persistent:
Bud:
*Shape.*—Ovate
*Length.*—Approximately 1.8 cm. .
*Diameter.*—Approximately 0.6 cm.
*Color.*—Near RHS Greyed-Purple N186B.
Flower size:
*Diameter.*—Approximately 3 cm.
*Flower tube length.*—Approximately 3 cm.
*Flower tube diameter at distal end.*—Approximately 1.2 cm.
*Flower tube diameter at proximal end.*—Approximately 0.3 cm.
Petals:
*Length from throat.*—About 3 cm.
*Width.*—About 2.4 cm.
*Quantity.*—5, fused.
*Texture.*—Smooth.
*Apex.*—Truncate.
*Margin.*—Entire.
Color:
*When opening.*—Inner surface: Near RHS Purple N79C. Outer surface: Near RHS Purple 79C.
*Fully opened.*—Inner surface: Near RHS Purple N78A. Outer surface: Near RHS Purple 79D. Flower throat (inside): Near RHS Purple 79A. Flower tube (outside): Near RHS Purple 76A. Flower tube, vein: Near RHS Purple 79A. Petal color, fading to: Near RHS Purple N77A.
Calyx/sepals:
*Quantity per flower.*—5, fused at base.
*Shape.*—Oblong.
*Length.*—Approximately 1.6 cm.
*Width.*—Approximately 0.4 cm.
*Apex.*—Obtuse.
*Base.*—Fused.
*Margin.*—Entire.
*Texture.*—Pubescent.
*Color.*—Upper Surface: Near RHS Green 137A. Lower Surface: Near RHS Green 137C.
Peduncle:
*Length.*—Approximately 3.2 cm.
*Diameter.*—Approximately 0.2 cm.
*Color.*—Near RHS Green 143B.
*Orientation.*—Approximately 35 degree angle from stem.
Fragrance: Sweet, very faint.

REPRODUCTIVE ORGANS

Stamens:
*Number.*—5.
*Filament length.*—Approximately 0.9 cm.
Anthers:
*Length.*—Approximately 0.1 cm.
*Shape.*—Globular.
*Color.*—RHS Greyed-Purple N186B.
*Pollen.*—Moderate quantity, colored near RHS Greyed-Purple N187B.
Pistil:
*Number.*—1.
*Length.*—Approximately 0.9 cm.
*Style.*—Length: Approximately 0.5 cm. Color: Near RHS White N155D.

*Stigma.*—Shape: Oblate. Color: Near RHS Yellow-Green 145D. Ovary Color: Near RHS Yellow-Green 145C.

OTHER CHARACTERISTICS

Seeds and fruits: Not observed.

Disease/pest resistance: Neither resistant nor susceptible to normal diseases and pests of *Petunia*.

Temperature tolerance: The new variety tolerates temperatures between approximately 6° to 35° C.

What is claimed is:

1. A new and distinct cultivar of *Petunia* plant named 'Daiichi Bluette Purple2' as herein illustrated and described.

* * * * *